(12) United States Patent
Bhatia et al.

(10) Patent No.: US 10,579,959 B2
(45) Date of Patent: Mar. 3, 2020

(54) INTELLIGENT ROUTING OF RADIO-FREQUENCY IDENTIFICATION DATA

(71) Applicant: CERNER INNOVATION, INC., Kansas City, MO (US)

(72) Inventors: Sameer Bhatia, Omaha, NE (US); Robert E. Whited, Kansas City, MO (US); Zeke W. Holland, Brunswick, ME (US); John W. Easler, Mt. Holly, NC (US); John David L. Nolen, Prairie Village, KS (US); Kevin J. Emerson, Shawnee, KS (US); Lori N. Cross, Kansas City, MO (US); Brian L. Lucas, Shawnee, KS (US)

(73) Assignee: Cerner Innovation, Inc., Kansas City, KS (US)

(*) Notice: Subject to any disclaimer, the term of this patent is extended or adjusted under 35 U.S.C. 154(b) by 0 days.

(21) Appl. No.: 14/482,097

(22) Filed: Sep. 10, 2014

(65) Prior Publication Data
US 2016/0071053 A1    Mar. 10, 2016

(51) Int. Cl.
*G06Q 10/08*    (2012.01)
*G06Q 50/22*    (2018.01)

(52) U.S. Cl.
CPC ........... *G06Q 10/087* (2013.01); *G06Q 50/22* (2013.01)

(58) Field of Classification Search
CPC .......................... G06Q 10/087; G06Q 50/22
See application file for complete search history.

(56) References Cited

U.S. PATENT DOCUMENTS

| 5,920,871 A | 7/1999 | Macri et al. |
| 6,535,129 B1 | 3/2003 | Petrick |
| 6,611,206 B2 | 8/2003 | Eshelman et al. |

(Continued)

FOREIGN PATENT DOCUMENTS

| EP | 1717571 A2 | 11/2006 |
| EP | 2239554 A1 | 10/2010 |

(Continued)

OTHER PUBLICATIONS

Dako partners with General Data to increase patient safety, Dako Denmark A/S, Jan. 28, 2008, Glostrup, Denmark, 2 pages. http://www.marketwired.com/press-release/dako-partners-with-general-data-to-increase-patient-safety-814514.htm.

(Continued)

*Primary Examiner* — Thien M Le
*Assistant Examiner* — Asifa Habib
(74) *Attorney, Agent, or Firm* — Shook, Hardy & Bacon L.L.P.

(57) ABSTRACT

Methods, systems, and computer-readable media are provided for routing radio-frequency identification (RFID) location data from an RFID tag reader to a record-keeping unit. A first tagging entry is received from a first record-keeping unit. The information associated with the first tagging entry is stored in a data store. A first set of location data is received, indicating that the RFID tag of the first item has been read by an RFID tag reader. It is algorithmically determined that the received location data corresponds to the first tagging entry received from the first record-keeping unit. The first set of location data is communicated to the first record-keeping unit.

20 Claims, 8 Drawing Sheets

(56) References Cited

U.S. PATENT DOCUMENTS

| | | |
|---|---|---|
| 6,714,121 B1 | 3/2004 | Moore |
| 6,826,422 B1 | 11/2004 | Modell et al. |
| 6,924,908 B1* | 8/2005 | Kimia .................. H04N 1/6033 358/1.9 |
| 7,199,712 B2 | 4/2007 | Tafas et al. |
| 7,278,579 B2 | 10/2007 | Loffredo et al. |
| 7,468,161 B2 | 12/2008 | Reinhardt et al. |
| 7,470,401 B2 | 12/2008 | Morales |
| 7,544,953 B2 | 6/2009 | Goodman |
| 7,578,786 B2 | 8/2009 | Boulais et al. |
| 7,591,783 B2 | 9/2009 | Boulais et al. |
| 7,663,101 B2 | 2/2010 | Goodman |
| 7,760,428 B2 | 7/2010 | Sieckmann |
| 7,860,727 B2 | 12/2010 | Showalter et al. |
| 7,966,269 B2 | 6/2011 | Bauer et al. |
| 7,978,062 B2 | 7/2011 | LaLonde et al. |
| 8,000,773 B2 | 8/2011 | Rousso et al. |
| 8,041,582 B2 | 10/2011 | Godschall et al. |
| 8,081,165 B2 | 12/2011 | Reiner |
| 8,118,732 B2 | 2/2012 | Banik et al. |
| 8,131,561 B2* | 3/2012 | Burke .................... G06Q 50/22 705/2 |
| 8,163,003 B2 | 4/2012 | Boyden et al. |
| 8,163,252 B2 | 4/2012 | Booker et al. |
| 8,234,128 B2* | 7/2012 | Martucci .............. A61B 5/0002 705/2 |
| 8,288,168 B2 | 10/2012 | Morales |
| 8,297,231 B2 | 10/2012 | Yanai et al. |
| 8,303,915 B2 | 11/2012 | Kram et al. |
| 8,315,445 B2 | 11/2012 | Sorenson et al. |
| 8,346,574 B2 | 1/2013 | Chirica et al. |
| 8,373,556 B2 | 2/2013 | LaLonde et al. |
| 8,380,541 B1 | 2/2013 | Holmes |
| 8,388,891 B2* | 3/2013 | Lefebvre ................ G01N 1/312 422/65 |
| 8,395,498 B2 | 3/2013 | Gaskill et al. |
| 8,632,994 B2 | 1/2014 | Winther et al. |
| 2002/0029156 A1 | 3/2002 | O'Dowd |
| 2005/0026117 A1* | 2/2005 | Judson .................. G06F 19/328 434/154 |
| 2005/0216313 A1* | 9/2005 | Claud .................... G06Q 50/22 705/3 |
| 2007/0067185 A1* | 3/2007 | Halsted ................. G06Q 50/22 705/2 |
| 2007/0187475 A1* | 8/2007 | MacLeod ............ G06F 19/3462 235/375 |
| 2008/0235055 A1 | 9/2008 | Mattingly et al. |
| 2008/0305515 A1 | 12/2008 | Burgart |
| 2009/0222746 A1* | 9/2009 | Chirica ................. G06F 19/327 715/762 |
| 2010/0088116 A1* | 4/2010 | Eisenberg .............. G06Q 50/24 705/3 |
| 2010/0167334 A1* | 7/2010 | Williamson, IV ..... G16H 10/40 435/29 |
| 2011/0217731 A1 | 9/2011 | Burgart et al. |
| 2012/0072452 A1* | 3/2012 | Stratman ................ G16H 10/40 707/772 |
| 2013/0027185 A1 | 1/2013 | Lavi |
| 2013/0159135 A1 | 6/2013 | Jones et al. |
| 2013/0166345 A1 | 6/2013 | Chirica et al. |
| 2015/0127368 A1* | 5/2015 | Greenberg ............ G01S 5/0263 705/2 |

FOREIGN PATENT DOCUMENTS

| | | |
|---|---|---|
| EP | 2165201 B1 | 2/2012 |
| EP | 2148204 B1 | 1/2013 |
| WO | 2005027014 A2 | 3/2005 |
| WO | 2007078842 A1 | 7/2007 |
| WO | 2008109672 A2 | 9/2008 |
| WO | 2008156566 A1 | 12/2008 |
| WO | 2011109769 A1 | 9/2011 |

OTHER PUBLICATIONS

German Researchers Create "Smart Test Tube" That Can Revolutionize Automated Clinical Pathology Laboratory Specimen Processing, Dec. 12, 2012, 5 pages. http://www.darkdaily.com/german-researchers-create-smart-test-tube-that-can-revolutionize-automated-clinical- pathology-laboratory-specimen-processing-1212#axzz2OliVefQ0.

ItemTracker Visual Sample Tracking and Management Software, 2013, ItemTracker Software Ltd., 1 page. http://www.itemtracker.com/.

Lou et al., A review of radio frequency identification technology for the anatomic pathology or biorepository laboratory: Much promise, some progress, and more work needed., Aug. 23, 2011, Journal of Pathology Informatics, 13 pages. http://www.ncbi.nlm.nih.gov/pmc/articles/PMC3162748/.

ODIN introduces EasySpecimen RFID-based Lab Tracking Solution, Apr. 18, 2011, Orlando, Florida, 2 pages. http://www.prweb.com/releases/2011/4/prweb8311787.htm.

Pathology Informatics 2014 Exhibitors, May 13-16, 2014, Pittsburgh, Pennsylvania, 3 pages. http://www.pathinformatics.pitt.edu/exhibitors?page=1.

Winsten, Dennis, RFID Economics, Aug. 16, 2011, 3 pages. http://laboratory-manager.advanceweb.com/Columns/Consultant-Corner/RFID-Economics.aspx.

* cited by examiner

INTELLIGENT ROUTING OF RADIO-FREQUENCY IDENTIFICATION DATA

BACKGROUND

When RFID technology is added to a system, such as a laboratory system, the RFID reader is typically directly coupled to the laboratory system. However, this makes it more difficult to swap RFID reader systems, and more difficult to leverage the RFID reader system to track other types of items. Additionally, the systems are often tied together such that only RFID technology can be used, and additional point-to-point connections may be incurred between the connected systems. For instance, in one embodiment, adding high volume RFID tracking of blood containers in Clinical Pathology on the same RFID reader system and direct connection as an existing setup of low volume tissue biopsies being tracked to Anatomic Pathology could result in less than 1% of the location updates received in the Anatomic Pathology system being for tissue biopsies. Or, a separate connection may be added to the RFID reader system and then both connections must then be filtered to the desired set of tags that need to cross the connection. This adds additional requirements to the RFID tag encodings to be able to embed information as to the type of item tagged to facilitate routing.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief and at a high level, this disclosure describes, among other things, methods, systems, and computer-readable media for intelligently routing radio-frequency identification (RFID) data from an RFID tag reader to a record-keeping unit based on the item associated with the RFID tag that was scanned. A central system, such as a bus, maintains a database of tagging entries that have been received from record-keeping units. The tagging entries indicate that an item, such as a laboratory specimen, has been tagged and may include data such as an identifier associated with the tagged item. When the central system receives data from an RFID tag reader indicating that a particular item's tag has been read, data, including location information, an identifier associated with the item, a time/date stamp, etc., is communicated to the central system for routing to the record-keeping unit(s) that has subscribed to this information. In one instance, a record-keeping unit has subscribed to receive this data if it sent a tagging entry to the central system indicating that it had tagged an item.

BRIEF DESCRIPTION OF THE DRAWINGS

Embodiments are described in detail below with reference to the attached drawings figures, wherein.

DETAILED DESCRIPTION

Figure 1:
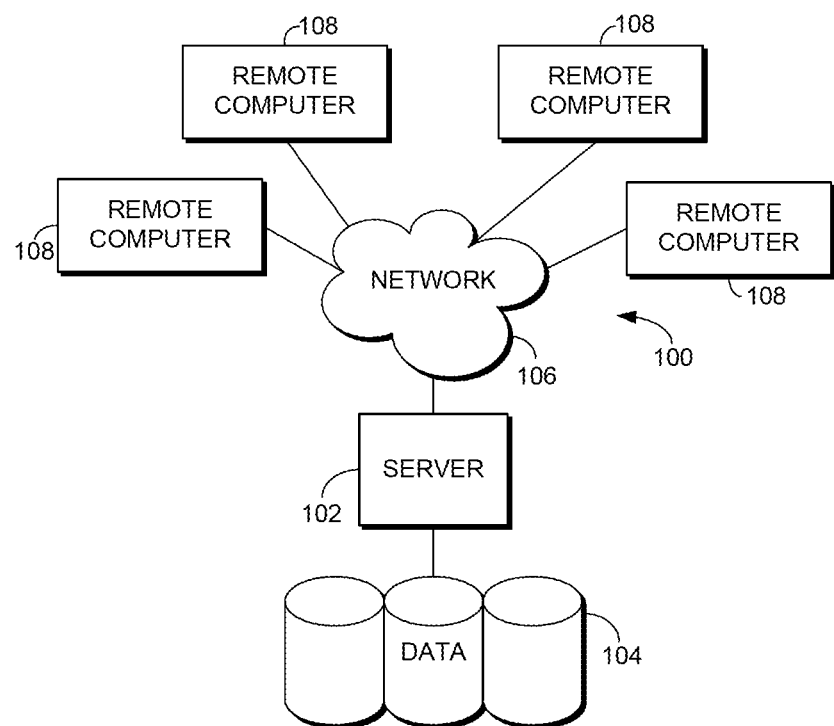
FIG. 1 is a block diagram of an exemplary computing system suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for end-to-end tracking for a particular item utilizing a technology that provides for the transfer of data. In one aspect, RFID technology is utilized to track a particular item through multiple locations over a period of time. A number of tag readers, such as RFID tag readers, may be utilized to read data from the RFID tag, including an identifier associated with the item. Data, including the identifier associated with the scanned/read item, location information where the item was scanned/read, a date/time stamp, and the like, may be communicated to a receiving system that has the capability of determining which of a plurality of systems has subscribed to receive updated information for that particular item. In one aspect, the item is a laboratory specimen and is tracked throughout its journey, from the sample being taken from a patient, to the sample being discarded after tests have been performed. For instance, the tracking may be accomplished using multiple readers, such as RFID tag readers that are located such that the RFID tag associated with the laboratory specimen can be read as it leaves the doctor's office or hospital, as it enters the laboratory, as it is tested, after it is tested, as it leaves the laboratory, as it is disposed, etc.

Time and location data associated with this process may be communicated to the system that subscribes to this type of information. For instance, record-keeping units, which may be laboratory systems or other such systems, may be used to monitor items that have been tagged with an RFID tag or some other type of tag or sensor. Each record-keeping unit may indicate to a central system that it has tagged a particular item with a tag, and that it would like to receive any updated data associated with that item. As such, when the tag associated with that particular item has been read by a tag reader, that updated information may be communicated to the central system in the form of a tagging entry so that the central system may determine to which record-keeping unit the updated data is to be sent. In aspects, the central system is coupled to a data store that stores the incoming tagging entries from the record-keeping units so that the central system knows which record-keeping unit has subscribed to updates from that particular item when updated information is received from a tag reader. In aspects, more than one record-keeping unit may subscribe to the same item, indicating that more than one unit wants to know when a location update is available.

Many advantages will become apparent, but to name a few, embodiments enable a reduced number of connections. Point-to-point connections between the record keeping units are unnecessary. Each record-keeping unit has a single connection to the central system, and thus does not have a direct connection to the RFID reader system. Additionally, an RFID reader system can be swapped for another without having to change the communication component to each record-keeping unit. Also, the record keeping units are not directly tied to an RFID reader system, allowing location updates to be provided from varying sources of RFID active tags, RFID passive tags, as well as non-RFID systems, such as barcode scanners. By enabling a centralized processing unit to identify a laboratory item of interest to the record-keeping units, the RFID reader system can also track non-laboratory items without impacting the record-keeping units. RFID tags tracked by the system are only required to contain unique identifiers and are not required to contain item type identifiers for the purpose of routing. Further, the centralized processing unit can efficiently identify the item association for a location update without this processing always being distributed to every record-keeping unit. Even further, varying types of items can be tracked through the RFID reader system, such that a record-keeping unit is only notified of the types of items in which it is interested.

Other advantages include the centralized processing unit providing the ability to filter location updates from the record-keeping units based on an item not having reached an initiating location for the item route or having reached a terminating location. Also, the centralized processing unit provides the ability for multiple record-keeping units to receive a location update in an independent manner. For example, a first record-keeping unit may be tracking an item having reached a destination, while a second record-keeping unit may be tracking items received. The centralized processing unit also allows efficient translation of RFID reader identifiers to record-keeping unit location identifiers where this can be maintained centrally rather than distributed across the record-keeping units. Here, the translation is hidden from the record-keeping units to allow for seamless swapping of the RFID reader systems.

A first aspect is directed to a computerized method, carried out by at least one server having one or more processors, of routing RFID location data from one of a plurality of RFID tag readers to a record-keeping unit. The method includes receiving, from a first record-keeping unit, a first tagging entry indicating that a first item has been tagged with an RFID tag, the first tagging entry comprising at least an identifier associated with the first item. Further, the method includes storing the first tagging entry in a data store, receiving a first set of location data indicating that the RFID tag of the first item has been read by an RFID tag reader, algorithmically determining that the received first set of location data corresponds to the first tagging entry received from the first record-keeping unit, and communicating the first set of location data to the first record-keeping unit.

A second aspect is directed to a system for routing RFID location data from one of a plurality of RFID tag readers to a record-keeping unit. The system includes a communications component having one or more processors and one or more computer-readable storage media, and a data store coupled to the communications component, wherein the communications component: receives, from an RFID tag reader, data associated with an item that has been tagged with an RFID tag, the data comprising location data of the item. The communications component further determines to which record-keeping unit the data is to be communicated by accessing a data store that stores tagging entries that correspond to items that have been tagged with an RFID tag, the tagging entries each comprising at least an identifier associated with a corresponding item, and from the data store, determining that a first record-keeping unit is to receive the data associated with the item. Further, the communications component communicates the data to the first record-keeping unit.

A third aspect is directed to one or more computer-readable media having computer-executable instructions embodied thereon that, when executed, facilitate a method of routing RFID location data from one of a plurality of RFID tag readers to a record-keeping unit. The method includes receiving a plurality of tagging entries from one or more record-keeping units, wherein each of the plurality of tagging entries indicates a lab specimen that has been associated with an RFID tag, and wherein each comprises an identifier associated with its respective lab specimen. Further, the method includes storing the plurality of tagging entries in a look-up table, and receiving location data from a processing unit that receives location data from a plurality of RFID tag readers. The receiving of the location data indicates that a first RFID tag of a first lab specimen has been read by an RFID tag reader, the received location data comprising a first identifier associated with the first lab specimen. Additionally, the method includes determining, based at least on accessing the look-up table, whether the first identifier matches any of the identifiers of the plurality of tagging entries stored in the look-up table. If the first identifier matches any of the identifiers in the look-up table, the method includes identifying the record-keeping unit that sent the tagging entry associated with the matching identifier, and communicating the location data to the identified record-keeping unit. However, if the first identifier does not match any of the identifiers in the look-up table, the method comprises querying the one or more record-keeping units to determine which of the one or more record-keeping units is associated with the first identifier.

Referring to the drawings in general, and initially to FIG. 1 in particular, an exemplary computing system environment, for instance, a medical information computing system, on which embodiments of the present invention may be implemented is illustrated and designated generally as reference numeral 100. It will be understood and appreciated by those of ordinary skill in the art that the illustrated medical information computing system environment 100 is merely an example of one suitable computing environment and is not intended to suggest any limitation as to the scope of use or functionality of the invention. Neither should the medical information computing system environment 100 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 100 includes a general purpose computing device in the form of a server 102. Components of the server 102 may include, without limitation, a processing unit, internal system memory, and a suitable system bus for coupling various system components, including database cluster 104, with the server 102. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 102 typically includes, or has access to, a variety of computer readable media, for instance, database cluster 104. Computer-readable media can be any available media that may be accessed by server 102, and includes volatile and nonvolatile media, as well as removable and non-removable media. By way of example, and not limitation, computer readable media may include computer storage media and communication media. Computer storage media may include, without limitation, volatile and nonvolatile media, as well as removable and non-removable media implemented in any method or technology for storage of information, such as computer-readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 102. Computer storage media does not comprise signals per se. Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer-readable media.

The computer storage media discussed above and illustrated in FIG. 1, including database cluster 104, provide storage of computer-readable instructions, data structures, program modules, and other data for the server 102.

The server 102 may operate in a computer network 106 using logical connections to one or more remote computers 108. Remote computers 108 may be located at a variety of locations in a medical or research environment, for example, but not limited to, clinical laboratories, hospitals and other inpatient settings, veterinary environments, ambulatory settings, medical billing and financial offices, hospital administration settings, home health-care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 108 may also be physically located in non-traditional medical care environments so that the entire health care community may be capable of integration on the network. The remote computers 108 may be personal computers, servers, routers, network PCs, peer devices, other common network nodes, or the like, and may include some or all of the components described above in relation to the server 102. The devices can be personal digital assistants or other like devices.

Exemplary computer networks 106 may include, without limitation, local area networks (LANs) and/or wide area networks (WANs). Such networking environments are commonplace in offices, enterprise-wide computer networks, intranets, and the Internet. When utilized in a WAN networking environment, the server 102 may include a modem or other means for establishing communications over the WAN, such as the Internet. In a networked environment, program modules or portions thereof may be stored in the server 102, in the database cluster 104, or on any of the remote computers 108. For example, and not by way of limitation, various application programs may reside on the memory associated with any one or more of the remote computers 108. It will be appreciated by those of ordinary skill in the art that the network connections shown are exemplary and other means of establishing a communications link between the computers (e.g., server 102 and remote computers 108) may be utilized.

In operation, a user may enter commands and information into the server 102 or convey the commands and information to the server 102 via one or more of the remote computers 108 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 102. In addition to a monitor, the server 102 and/or remote computers 108 may include other peripheral output devices, such as speakers and a printer.

Although many other internal components of the server 102 and the remote computers 108 are not shown, those of ordinary skill in the art will appreciate that such components and their interconnection are well known. Accordingly, additional details concerning the internal construction of the server 102 and the remote computers 108 are not further disclosed herein.

Figure 2:
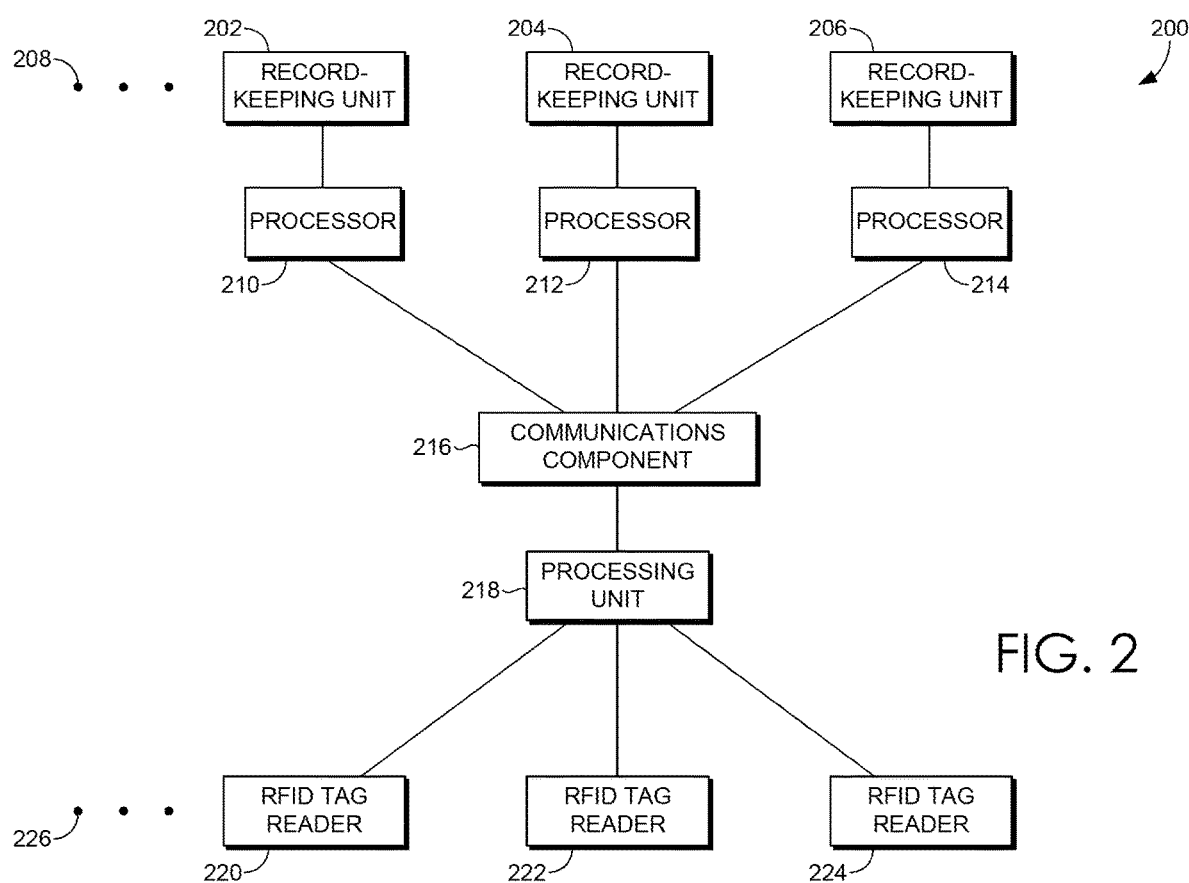
FIG. 2 depicts an exemplary system architecture suitable for implementing embodiments of the present invention.

Turning now to FIG. 2, an exemplary system architecture 200 suitable for implementing embodiments of the present invention is illustrated. It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by one or more entities may be carried out by hardware, firmware, and/or software. For instance, various functions may be carried out by a processor executing instructions stored in memory.

Among other components not shown, the system 200 may include a number of record-keeping units 202, 204, and 206. While three record-keeping units are illustrated in the embodiment of FIG. 2, item 208 indicates that there may be additional record-keeping units utilized in other embodiments. Record-keeping units, as used herein, are systems that are coupled to a data store for retrievably storing information. Record-keeping units may each store the same type of information, or each may store different types of information. For instance, not all of the record-keeping units 202, 204, and 206 need to be within the same industry. Using embodiments described herein, the communications component 216 is capable of determining which record-keeping unit needs received location data, and as such, the record-keeping units could store entirely different types of data.

As mentioned, the record-keeping units 202, 204, and 206 may be used in a variety of industries. For example, in the healthcare industry, the record-keeping units 202, 204, and 206 may be laboratory systems that store patient data, such as electronic medical records (EMRs). As such, in one embodiment, the items being tagged are laboratory specimens, such as a blood sample, a biopsy, a surgical specimen, or some other anatomical specimen. The patient data may also include tests that are to be performed on patients, outcomes of these tests, and other data relating to procedures, biopsies, surgical specimens, etc. More specifically, in one embodiment, a portion of the data stored by way of the record-keeping units 202, 204, and 206 may be information that indicates the past and current location of a particular lab specimen, such as before it is transported to a pathology laboratory, during its time in the laboratory, and after it has been tested and even discarded.

There are many ways the location and other data associated with lab specimens and other objects can be tracked. Various sensors and tags are currently available that can be used to provide this tracking functionality. The sensors/tags may utilize any real-time location services technology such as ultrasound technology, infrared technology, radio-frequency identification (RFID) technology, or the like. More details regarding the sensors/tags used on items (e.g., lab specimens) will be discussed in more detail below.

In aspects, RFID technology is utilized. As such, in this aspect, the tags that are coupled to the items to be tracked are RFID tags that are capable of being read by an RFID tag reader. Generally, RFID technology refers to the wireless non-contact use of RF electromagnetic fields for the transfer of data. One use of RFID technology is to automatically identify and track tags attached to different objects. The tags contain electronically stored information and may be powered by and read at short ranges via magnetic fields. Others may use a different power source, such as a battery, etc. Tags may also be embedded in a tracked object. Because of the versatility of RFID technology, aspects may be used to track and manage inventory, assets, animals, etc. Exemplary industries that may utilize aspects described herein include automobile production to track parts through an assembly line, pharmaceutical warehousing, animal identification, laboratory specimen tracking through a laboratory testing process, etc.

As used herein, a tag is a label that is attached to an item to be identified and tracked. RFID tags may be passive or active. An active tag may have a battery and periodically transmits its ID signal. Another type of active tag may also have a battery, but the battery is only activated in the presence of an RFID reader. The tags described herein may be active in one aspect but passive in an alternative aspect.

Each record-keeping unit 202, 204, and 206 may be associated with and coupled to a processor, such as processors 210, 212, and 214 that are generally responsible for determining that an item has been associated with a sensor/tag. For instance, in the case that record-keeping unit 202 tags a lab specimen with an RFID tag, the processor 210 saves this information (e.g., an identifier associated with the lab specimen and the RFID tag) and communicates the information to the communications component 216. The processors 210, 212, and 214 may also be queried by the communications component 216 once location data has been sent by an RFID tag reader in the case that the communications component 216 is unable to determine to which record-keeping unit the received location data is to be sent. This will also be discussed in more detail herein.

The communications component 216 is generally responsible for receiving large amounts of data from the processing unit 218, which receives data from a number of sensor/tag readers, such as RFID tag readers 220, 222, and 224. While three RFID tag readers are illustrated in FIG. 2, more tag readers may be utilized, as represented by item 226. While the readers are labeled as RFID tag readers, they may additionally or alternatively utilize another technology, such as one described above. The RFID tag readers 220, 222, and 224 may be located, for example, in a doorway, at the entrance or exit to a building, on a piece of laboratory equipment, or the like. In one embodiment, if the location of a lab specimen sent to a pathology laboratory is being tracked, the RFID tag of that particular lab specimen may be read by a tag reader as the specimen exits the doctor's office or hospital, as the specimen enters the laboratory, just before the specimen is tested by a particular piece of lab equipment, after the test has been performed, as the specimen exits the laboratory, as the specimen is being discarded, etc. These are solely examples for a lab specimen, but if the item is something other than a lab specimen, the locations of the tag readers would vary. Any and all such possible locations are contemplated to be within the scope of aspects described herein. In an embodiment, neither the processing unit 218 nor the RFID tag readers 220, 222, and 224 are associated with a particular record-keeping unit 202, 204, or 206.

The data collected by the RFID tag readers 220, 222, and 224 may include, for instance, a location of the tag reader that read the item's tag, a date/time stamp, and identifier associated with the item of the tag that was read, etc. While this data may be referred to as location data, it should be noted that this data may also include other types of data, such as those mentioned above. In real time, each tag reader may communicate its data from reading an item's tag to a processing unit 218 that processes the data prior to the data being communicated to the communications component 216. In one aspect, the processing unit 218 may be responsible for sorting the data by item identifier. For instance, hundreds, thousands, etc. of sets of data may be received by the processing unit 218 at any time. Because of the potential of large amounts of data, the processing unit 218 may provide sorting capabilities so that the data communicated to the communications component 216 is organized by identifier. In another embodiment, the processing unit 218 may solely be responsible for receiving data from the RFID tag readers 220, 222, and 224 and "dumping" the data to the communications component 216 such that the communications component 216 would be responsible for sorting and further organizing the data.

The RFID tag readers 220, 222, and 224 may be active or passive. Passive readers receive radio signals from active tags. Active readers may transmit interrogator signals and may also receive authentication replies from passive tags. Another type of active tag uses active tags awoken with an interrogator signal from the active reader.

In one embodiment, communications component 216 is a bus, such as the bus described above with respect to FIG. 1. As referred to herein, a bus is a communication system that is generally responsible for transferring data between various components inside of a computer, or even between computers. In one embodiment, the communications component 216 utilizes Cerner CareAware iBus® software. However, the type of component used to perform the functions described herein with respect to the communications component 216 may vary, and those other types of components are contemplated to be within the scope of aspects described herein.

Figure 5:
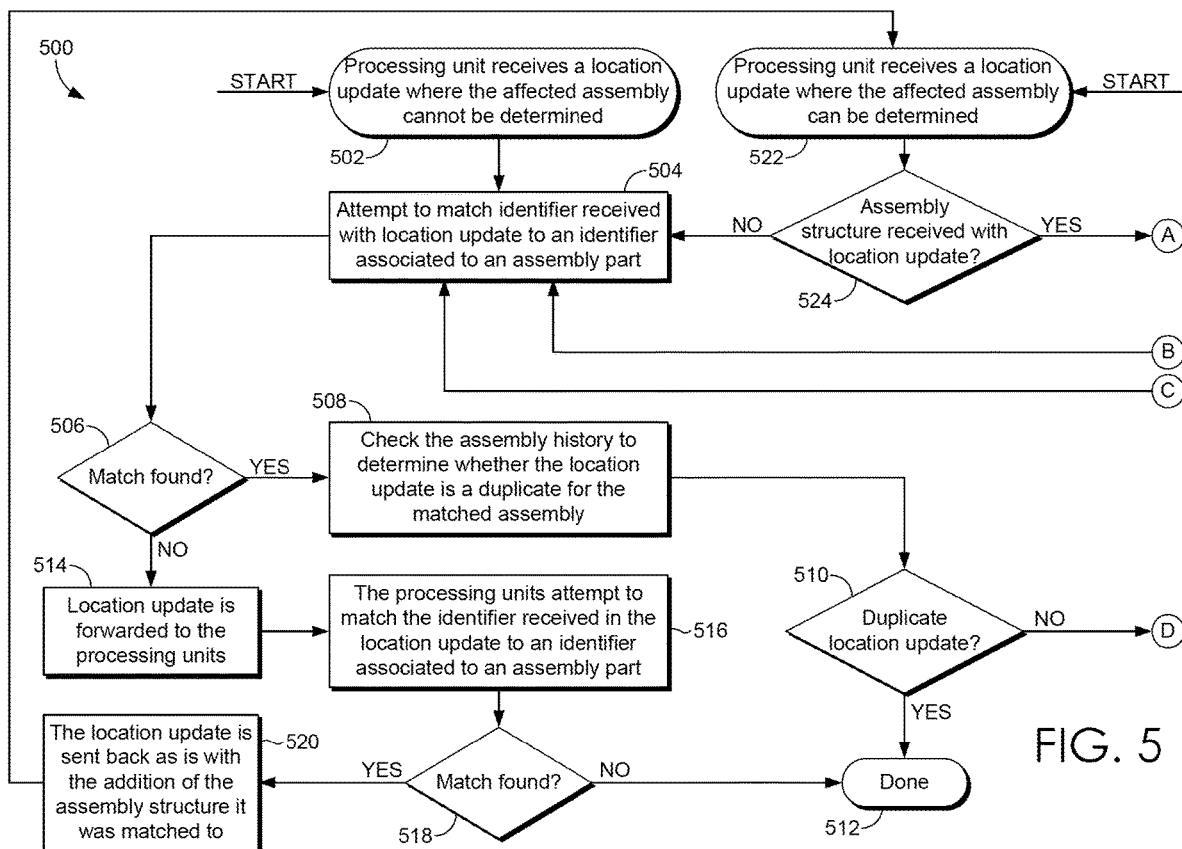
FIG. 5 depicts a flow diagram of an exemplary algorithm for carrying out embodiments of the present invention.
Figure 5:
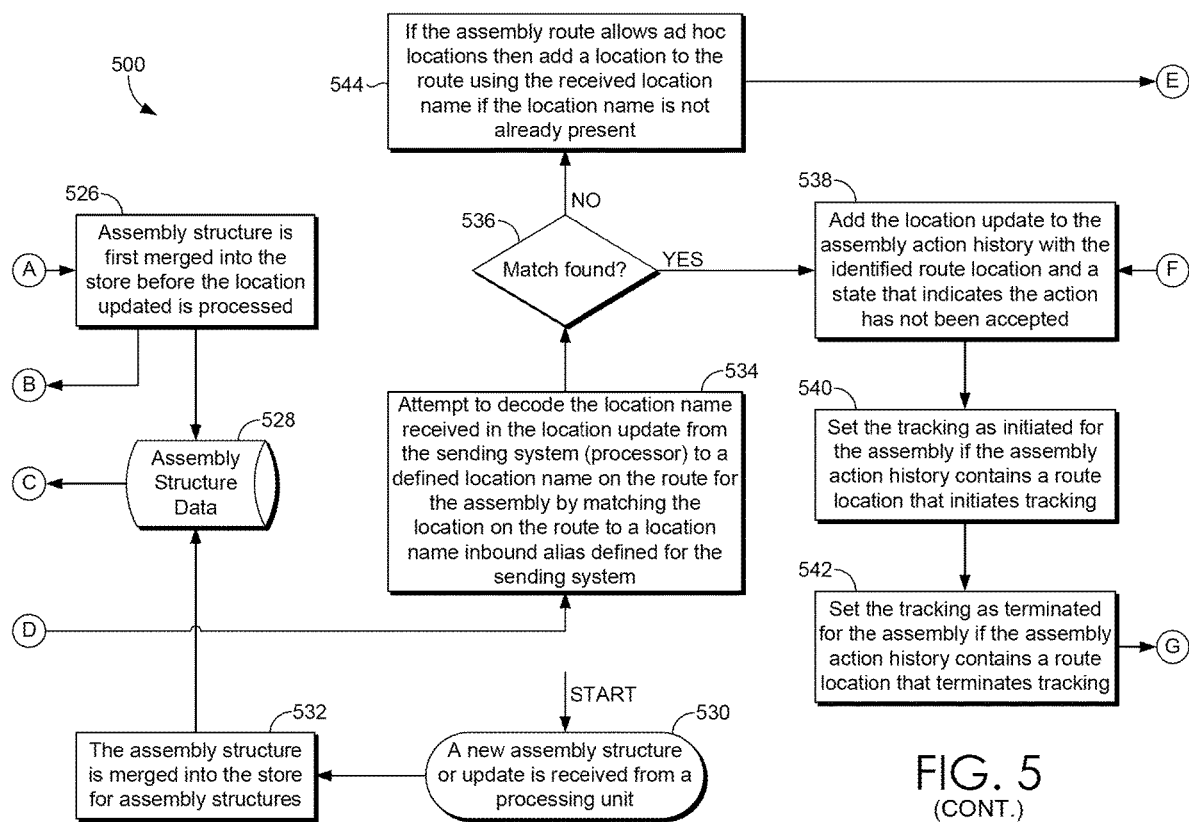
Figure 5:
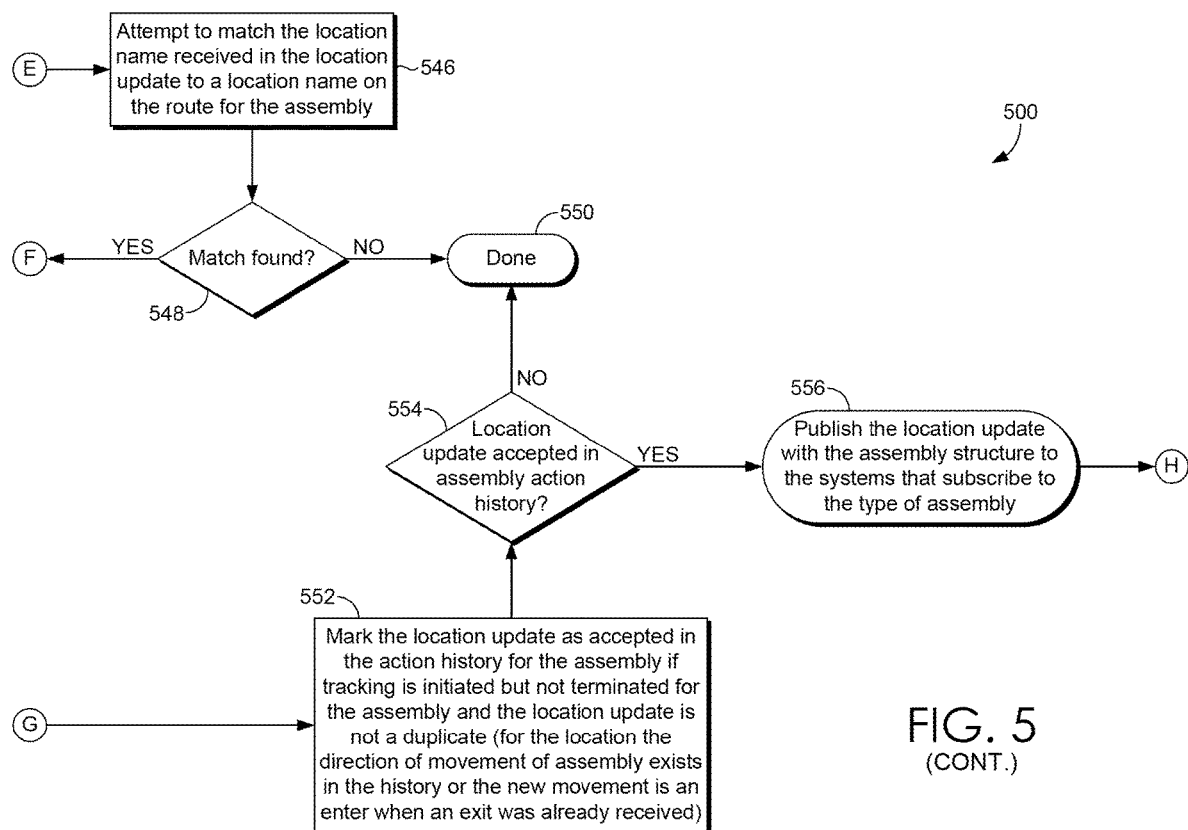
Figure 5:
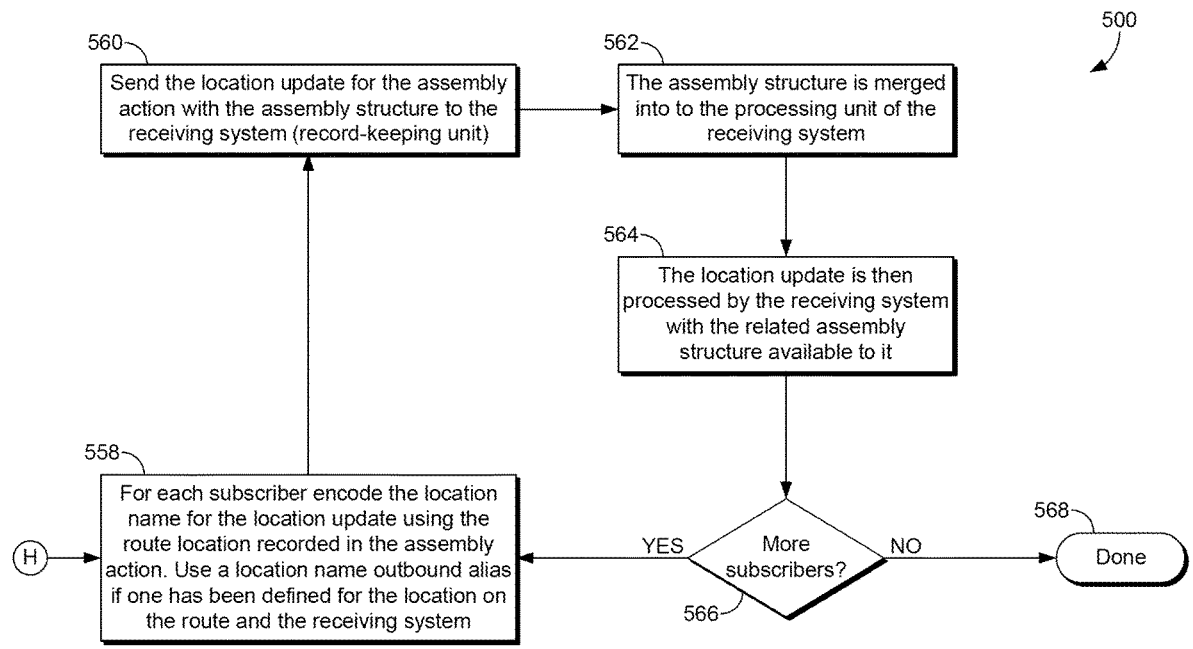

Whether the processing unit 218 sorts/parses the data or not, communications component 216 may determine to which record keeping unit 202, 204, and/or 206 the data is to be sent. Without utilizing aspects described herein, all received data from the tag readers would be communicated to each of the record-keeping units, as there would not be logic incorporated to determine which record-keeping unit is responsible for keeping track of the tracking of which items. Referring to FIG. 5, a flow diagram of an exemplary algorithm for carrying out embodiments of the present invention is depicted. In one aspect, the communications component 216 has logic stored thereon for carrying a decision-making algorithm, such as the algorithm shown in FIG. 5. The steps shown in FIG. 5 are exemplary in nature and in no way are meant to limit embodiments provided herein.

Blocks 502, 504, 506, 508, 510, 512, 514, 516, 518, 520, 522, and 524 of FIG. 5 describe the portion of the exemplary algorithm where, in this embodiment, an assembly tracking component receives data, such as a location update, but the affected assembly cannot be determined, or, alternatively, where the affected assembly can be determined. The algorithm indicates that a match is attempted to be found between the identifiers. Where a match is found, it is determined whether the location update is a duplicate. In some aspects, multiple instances of the same location update may be received, and as such, to avoid having duplicate entries, it may be determined whether a received location update is a duplicate. Blocks 526, 528, 530, 532, 534, 536, 538, 540, 542, and 544 represent the portion of the exemplary algorithm where a location name received in the location update is decoded, and it is determined whether there is a match between a location name already stored and the location name decoded from the location update. Blocks 546, 548, 550, 552, 554, and 556 represent the portion of the exemplary algorithm where it is determined whether the location update is accepted in the assembly action history. If so, the location update is published. Blocks 558, 560, 562, 564, 566, and 568 represent the portion of the exemplary algorithm where the location update data is sent to the receiving system, such as the communications component 216 of FIG. 2. The receiving system processes the location update and determines which subscribers, such as which of the record-keeping units 202, 204, and 206, subscribe to the data of the particular item whose tag has been scanned.

Returning now to FIG. 2, once the communications component 216 has determined, such as by an algorithm or other logic, to which record-keeping unit(s) the data is to be sent, the data is sent. This allows the record-keeping units 202, 204, and 206 to update their respective records as to where a particular item is located at a particular time. This may be particularly useful when the item is a laboratory specimen that has particular time constrains as to how long the laboratory has before the specimen is no longer able to be tested (e.g., before the specimen "expires").

Figure 3:
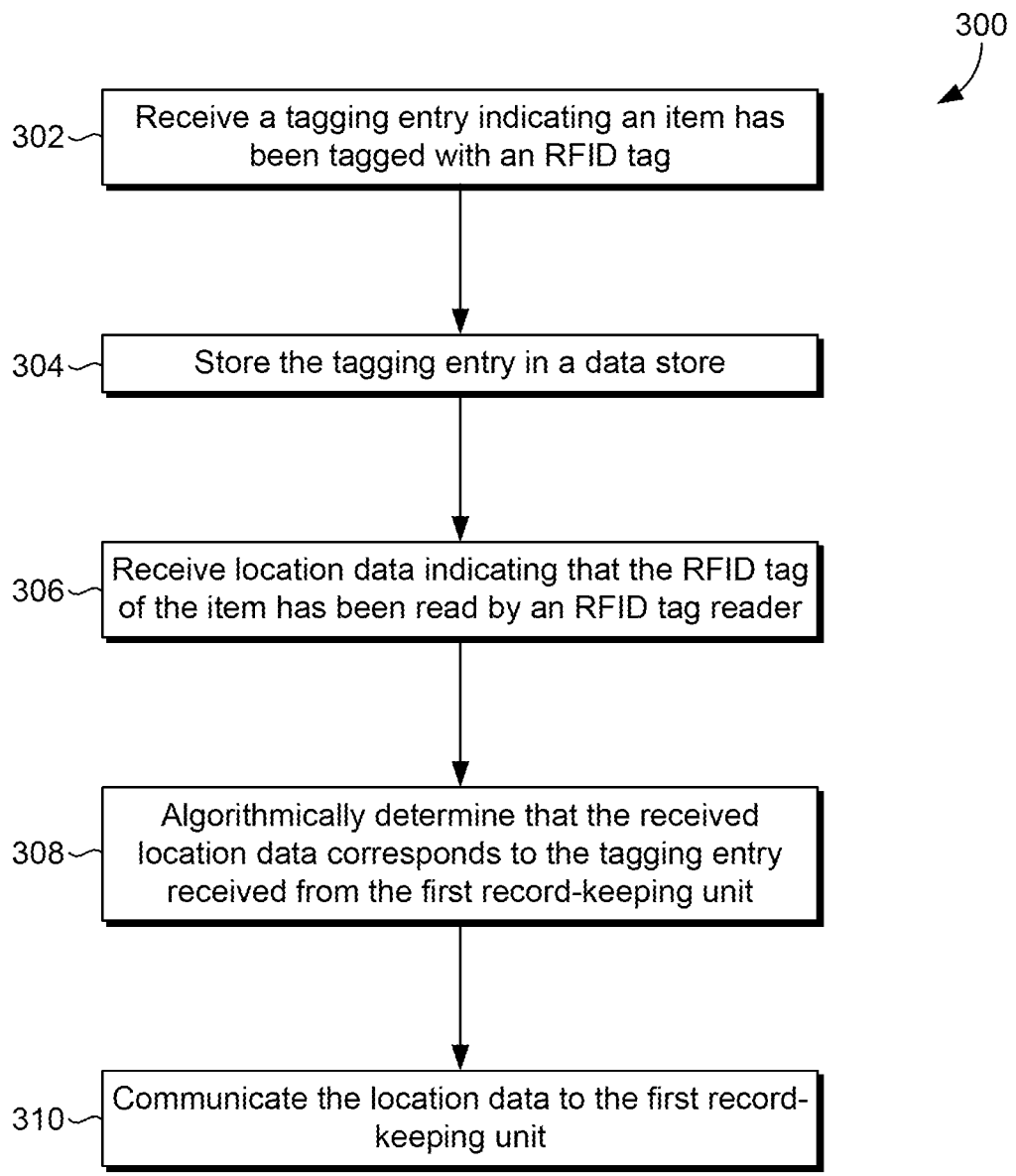
FIG. 3 depicts a flow diagram of a method for routing RFID location data from one of a plurality of RFID tag readers to a record-keeping unit, in accordance with an embodiment of the present invention.

FIG. 3 depicts a flow diagram of a method 300 for routing RFID location data from one of a plurality of RFID readers to a record-keeping unit, in accordance with an embodiment of the present invention. At block 302, a tagging entry is received indicating that an item has been tagged with an RFID tag. In one aspect, the tagging entry is received at a central system, such as the communications component 216 of FIG. 2. At block 304, the tagging entry is stored by the central system in a data store. In one embodiment, the received tagging entry is stored in a look-up table that may store, for example, an identifier associated with the item to be tracked, and data corresponding to the RFID tag. Location data is received at block 306, the location data indicating that the RFID tag of the item has been read by an RFID tag reader. The location data may include, for exemplary purposes only, a location of the tag reader that read the tag, an identifier associated with the tagged item, a date/time stamp of the reading of the tag, or the like.

At block 308, it is algorithmically determined that the received location data corresponds to the tagging entry received from a first record-keeping unit. In one aspect, the record-keeping unit is a laboratory system that stores held data for a plurality of patients (e.g., electronic medical records). Once determined, the location data is communicated to the first record-keeping unit at block 310. An algorithm, such as the algorithm described above with respect to FIG. 5, may be utilized by the central system (e.g., the communications component 216 of FIG. 2) to determine which record-keeping unit has subscribed to an item, and thus to which unit the location data is to be communicated. In one aspect, the algorithmic determining may comprise accessing a look-up table in the data store and from the look-up table, identifying the tagging entry that comprises the identifier associated with the item. For a match to exist, the identifier associated with the location data may be the same as the identifier associated with the item.

In one embodiment, the item described above is a first item, the tagging entry is a first tagging entry, etc. In such an embodiment, a second tagging entry may be received from a second record-keeping unit, the second tagging entry indicating that a second item has been tagged with an RFID tag. The second tagging entry may comprise at least an identifier associated with the second item. The second tagging entry, like the first tagging entry, may be stored in the data store. A second set of location data is received indicating that the RFID tag of the item has been read by an RFID tag reader. The second set of location data includes an identifier associated with an item. It can then be determined, by way of accessing the data store, whether the second set of location data corresponds to the first tagging entry or the second tagging entry. In particular, a look-up table may be utilized that stores a plurality of tagging entries associated with identifiers of items that are to be tracked by way of a plurality of RFID tag readers. It is then determined whether a match exists between the identifier of the second set of location data and the identifier of one of, at least, the first tagging entry or the second tagging entry.

Figure 4:
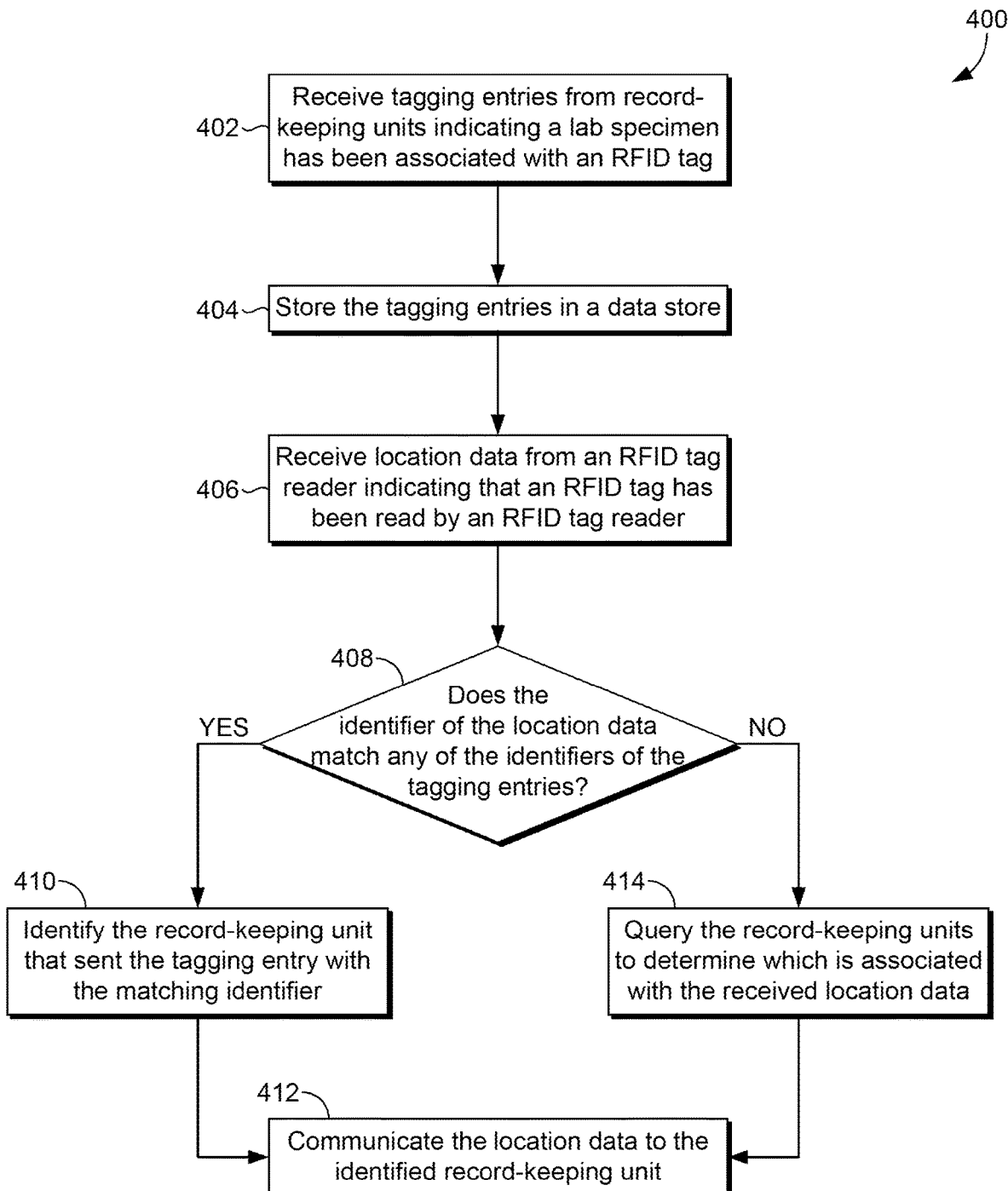
FIG. 4 depicts a flow diagram of another method for routing RFID location data from one of a plurality of RFID tag readers to a record-keeping unit, in accordance with an embodiment of the present invention.

FIG. 4 depicts a flow diagram of another method 400 for routing RFID location data from one of a plurality of RFID readers to a record-keeping unit, in accordance with an embodiment of the present invention. The method 400 of FIG. 4 is specifically directed to the use of aspects described herein for lab specimens in the healthcare industry. This is just one example and is not intended to limit the scope of other aspects described herein. At block 402, tagging entries are received from record-keeping units indicating that a lab specimen has been associated with an RFID tag. Each tagging entry may comprise an identifier associated with its respective lab specimen. At block 404, the tagging entries are stored in a data store. At block 406, location data is received from an RFID tag reader indicating that an RFID tag has been read by an RFID tag reader. At block 408, it is determined whether the identifier of the location data matches any of the identifiers of the tagging entries. This could be determined by, for instance, identifying the record-keeping unit that sent the tagging entry associated with the matching identifier and communicating the location data to the identified record-keeping unit. If the identifier of the location data matches any of the identifiers of the tagging entries, the record-keeping unit that sent the tagging entry with the matching identifier is identified at block 410. The location data is then communicated to the identified record-keeping unit at block 412.

If the identifier of the location data does not match any of the identifiers of the tagging entries, the record-keeping units may be queried at block 414 to determine which is associated with the received location data. In one aspect, if the querying of the record-keeping units does not result in an identification of the unit that sent the tagging entry or that otherwise subscribes to the updated data (e.g., location data) of the particular lab specimen, the location data may be discarded. Additionally, it may be determined if the received location data is a duplicate of location data that has already been received (e.g., that is already stored in the data store or stored by the respective record-keeping unit), the location data may also be discarded.

While embodiments have been described as to the functionality of the tracking system, various use cases will not be detailed. Initially, one use case is for tracking a dashboard with alerts. This may allow an end user to automatically know how many specimens are waiting to be picked up. This information can be updated automatically based on the number of specimens that remain. The end user in the clinic or at the point of collection may place the RFID-labeled specimen on an RFID tag reader. Alternatively, an RFID mobile device may be used to read the number of specimens. In a related aspect, as the specimen enters a laboratory, an RFID tag reader may automatically enable a login to a laboratory system.

In another aspect, embodiments may be used for the automatic discard of specimens. Each specimen may have a certain period of time after which it is to be discarded. Utilizing RFID technology or the like, it may be determined at which time the source of the specimen was taken. Utilizing an algorithm, it can then be determined when the specimen is to be discarded (e.g., based on an "expiration" of the specimen). This process could be robotic or manual. If robotic, a robotic arm could communicate with the discard module to discard specimens without human intervention. If manual, a human may utilize a mobile device to scan the storage area. An alert or trigger may notify the end user that the specimen is ready to be discarded. A technician or other healthcare professional may check that all materials meet the discard criteria (e.g., retention period has passed, case not amended, case not marked "do-not-discard"). It may then alert the user to any materials in the batch that should not be discarded and would update the status of the remaining materials to be discarded.

In another aspect, the technology described herein may be used for auto archiving of slides utilizing robotics.

In yet another aspect, a patient's RFID armband could be auto verified with auto print verification. For example, a patient may check into a hospital or laboratory and receive an armband equipped with an RFID tag. The patient then enters the laboratory. At the time the patient receives a biopsy or blood draw, the technician (e.g., nurse) may utilize an RFID reader to print an RFID patient chart label. The label is then affixed to the specimen/blood tube.

In yet another aspect, an RFID label may be affixed to a blood tube, a formalin filled container, tissue cassettes, and slides. These items may be tracked from grossing to histology, into the tissue processor, out of the tissue processor, all without any human action other than putting the item on/near a reader. Similarly, for slides, case assembly, slide delivery, and slide return could be done without the need to scan each slide individually.

Another aspect enables the ability to track multiple RFID unique identifiers with a single accession number. Many times there are multiple specimens per patient. The specimens may all be associated with a single accession number. Pairing multiple specimens with individualized RFID unique identifiers to one accession number provides granular level data on patient biopsies.

Yet another aspect provides for route optimization for courier pickup and drop offs. Data for each location requiring a pickup may be passed to a route optimization engine periodically throughout the workday to generate optimized routes for only those locations where pickups are known to be required. This may eliminate a significant number of "dry" or non-essential stops, which may end up being 40-60% of all courier stops.

Still yet, an aspect enables for tracking pathology slide trays using RFID technology. An assembly tracking system may track at the slide tray level. A unique identifier could be paired to all accession numbers on each individual slide.

One other aspect allows for the system described herein to be used with both native and foreign (e.g., third-party) systems. Record keeping units may have records on the items being tracked that describe the assembled structure of the items (referred to as assemblies). But here, embodiments described herein provide the processor of the record keeping unit to have something like a reverse staging area (e.g., processors 210, 212, and 214 of FIG. 2) for the assembled items, where the data is stored in a consistent manner (database schema). This provides the ability to gather very basic information as to which parts were assembled into an item and their identifiers (e.g., unique identifiers, tags, record identifiers) so that data is consistently sent and received. Each RFID tag may contain any tag encoding scheme. A processing component, such as processing unit 218 of FIG. 2 may be used to track RFID tags that are read by RFID tag readers across a large geographical area.

By pushing the identifiers for the assembled parts on an item to the staging area, the assembly can be identified such that a given record keeping unit only receives location data for which it contains the information of the assembled item in the reverse staging area. Without knowing whether a record keeping unit will recognize a tag (e.g., electronic product code (EPC) tag) would cause a record keeping unit to do extra processing for the tags it does not recognize, and may even require multiple record keeping units to perform RFID tag lookups on the same tag unnecessarily.

By creating publications for assembled items by the publishing record keeping unit, other record keeping units may subscribe to the publishing to receive copies of the information into their processors. This enables other record keeping units to know what is in route, provides for the ability to augment the assembly information, and for the ability of the location data to go to multiple record keeping units.

Additionally, by pushing the identifiers to the staging area (e.g., processor 210, 212, or 214 of FIG. 2), the assembly tracking data can be queried by any set of identifiers of which the identifiers for a given assembly can be submitted from multiple record keeping units. In the case of lab systems, this may allow a user of, for example, a given lab system to query by identifiers that were assigned by another lab system.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. A computerized method, carried out by at least one server having one or more processors, of routing radio-frequency identification (RFID) location data for an item tagged with a RFID tag from one of a plurality of RFID tag readers to at least one of a plurality of record-keeping units, the method comprising:

receiving an indication from a first record-keeping unit that a first item has been tagged with an RFID tag;

in response to receiving the indication from the first record-keeping unit, generating a first tagging entry comprising an identifier associated with the first item, the first tagging entry being stored in a database associated with a central server;

receiving one or more location data subscription requests corresponding to the first item from a set of record-keeping units of a plurality of record-keeping units;

in response to receiving one or more location data subscription requests, subscribing the set of record-keeping units to receive location data for the first item, wherein the one or more location data subscription requests corresponding to the first item indicates to the central server that location data received that corresponds to the identifier associated with the first item is to be communicated to the set of record-keeping units, and wherein each record-keeping unit maintains a record of subscribed item locations in a local database;

receiving, by the central server, a first set of location data indicating that the RFID tag of the first item has been read by an RFID tag reader;

determining, by the central server, that the first set of location data corresponds to the first tagging entry received from the first record-keeping unit;

based upon determining that the first set of location data corresponds to the first item, communicating, by the central server and only to the set of record-keeping units, the first set of location data;

updating the record associated with the first item in the local database of each record-keeping unit of the set of record-keeping units; and when the RFID tag of the first item does not match any of the tagging entries in the database, querying by the central server each of the set of record-keeping units to determine which of the plurality of record-keeping units is associated with the RFID tag of the first item.

2. The method of claim 1, wherein the first set of location data comprises:

(1) a location of the RFID tag reader that read the RFID tag of the first item, and (2) the identifier associated with the first item.

3. The method of claim 2, wherein the determining comprises:

accessing a look-up table in the database; and from the database, identifying the first tagging entry that comprises the identifier associated with the first item, the identifier associated with the first item matching with the identifier of the received first set of location data.

4. The method of claim 1, wherein the first record-keeping unit is a laboratory system that stores health data for a plurality of patients.

5. The method of claim 1, wherein the first record-keeping unit stores electronic medical records for a plurality of patients.

6. The method of claim 1, further comprising:

receiving, from a second record-keeping unit, a second tagging entry indicating that a second item has been tagged with an RFID tag, the second tagging entry comprising at least an identifier associated with the second item;

storing the second tagging entry in the database;

receiving a second set of location data indicating that the RFID tag of the item has been read by an RFID tag reader, the second set of location data comprising the identifier associated with the second item; and determining, by way of accessing the database, whether the second set of location data corresponds to the first tagging entry or the second tagging entry.

7. The method of claim 6, wherein the determining whether the second set of location data corresponds to the first tagging entry or the second tagging entry further comprises:

accessing a look-up table in the database, the look-up table comprising a plurality of tagging entries associated with identifiers of items that are to be tracked by way of a plurality of RFID tag readers, the plurality of tagging entries having been sent by the plurality of record-keeping units; and determining that a match exists between the identifier of the second set of location data and the identifier of one of the first tagging entry or the second tagging entry.

8. The method of claim 1, further comprising:

algorithmically determining that the received location data also corresponds to a second tagging entry received from a second record-keeping unit; and communicating the location data to the first record-keeping unit and the second record-keeping unit.

9. A system for routing radio-frequency identification (RFID) location data from one of a plurality of RFID tag readers to at least one record-keeping unit, the system comprising:

a plurality of record-keeping units, wherein each record-keeping unit of the plurality of record-keeping units maintains a record of subscribed item locations in a local database, wherein the local database is updated in response to receiving location data communicated by a central server;

a plurality of RFID tag readers;

the central server having a communications component, one or more processors and one or more computer-readable storage media; and a data store coupled to the central server, wherein the central server:

receives, from an RFID tag reader, data associated with an item that has been tagged with an RFID tag, the data comprising location data of the item;

identifies a set of record-keeping units the received data is to be communicated to by accessing the data store comprising tagging entries that correspond to items that have been tagged with an RFID tag, the tagging entries each comprising at least an identifier associated with a corresponding item, and that stores subscriptions received from the set of record-keeping units subscribing to received data corresponding to the identifier, wherein a subscription indicates that location data received and corresponding to the subscribed item is to be communicated to the subscribing record-keeping units, and wherein the set of record-keeping units comprises at least one of the plurality of record-keeping units;

communicates the data to the set of record-keeping units subscribed to an item; and when the data does not match any of the data in the data store, queries each of the set of record-keeping units to determine which of the plurality of record-keeping units is associated with the data.

10. The system of claim 9, further comprising a processing unit that receives data from the plurality of RFID tag readers and communicates the data to the communications component.

11. The system of claim 9, wherein the communications component is a bus.

12. The system of claim 10, wherein the communications component discards a portion of the data received from the plurality of RFID tag readers when none of the plurality of record-keeping units are subscribed to receive the portion of the data.

13. The system of claim 9, wherein the item is a laboratory specimen that is to be sent to a pathology laboratory for testing and processing.

14. One or more computer-readable media having computer-executable instructions embodied thereon that, when executed by one or more processors, facilitate a method of routing radio-frequency identification (RFID) location data of a RFID tagged lab specimen from one of a plurality of RFID tag reader positioned at various locations to at least one of a plurality of record-keeping units positioned at different locations, the method comprising:

adding a tagging entry to a look-up table having a plurality of tagging entries, wherein the tagging entry is received by a central server maintaining the look-up table and from a record-keeping unit of a set of record-keeping units, wherein each tagging entry of the plurality of tagging entries includes an identifier corresponding to an RFID tagged lab specimen;

adding a plurality of subscriptions to the look-up table, wherein each subscription is received by the central server from one of the set of record-keeping units, wherein each subscription of the plurality of subscriptions identifies a particular RFID tagged lab specimen for which location data received by the central server is to be communicated by the central server to the record-keeping unit sending the subscription, and wherein each record-keeping unit of the plurality of record-keeping units maintains a locally stored record of the location of one or more subscribed RFID tagged lab specimens;

based upon scanning a first RFID tagged lab specimen with a first RFID tag reader at a first location, communicating location data for the first RFID tagged lab specimen from the first RFID tag reader to the central server, the communicated location data comprising a first identifier associated with the first RFID tagged lab specimen;

based at least on accessing the look-up table, determining whether the first identifier matches any of the identifiers of the plurality of tagging entries in the look-up table;

responsive to determining the first identifier matches any of the identifiers in the look-up table, communicating the location data to any record-keeping units subscribing to the first identifier;

updating the locally stored record of each of the set of record keeping units associated with the first item; and when the first identifier does not match any of the identifiers in the look-up table, querying by the central server each of the set of record-keeping units to determine which of the plurality of record-keeping units is associated with the first identifier.

15. The media of claim 14, further comprising:

receiving, from a first record-keeping unit, a tagging entry indicating that a lab specimen has been associated with an RFID tag, the tagging entry comprising at least the first identifier associated with the lab specimen; and storing the tagging entry in the look-up table.

16. The media of claim 14, wherein the location data comprises:

(1) a location associated with the RFID tag reader that read the RFID tag of the first RFID tagged lab specimen, and (2) the first identifier associated with the first RFID tagged lab specimen.

17. The media of claim 14, wherein each of the one or more record-keeping units is a laboratory system that stores health data for a plurality of patients.

18. The media of claim 14, wherein the one or more record-keeping units store electronic medical records associated with a plurality of patients.

19. The media of claim 14, wherein if the querying of the one or more record-keeping units does not result in an identification of the record-keeping unit that sent the tagging entry associated with the matching identifier, discarding the location data received from the first RFID tag reader.

20. The media of claim 14, wherein the first RFID tagged lab specimen is one of a blood sample, a biopsy, a surgical specimen, or another anatomical specimen.

* * * * *